(12) United States Patent
Lee et al.

(10) Patent No.: US 6,420,543 B1
(45) Date of Patent: Jul. 16, 2002

(54) GROWTH DIFFERENTIATION FACTOR-15

(75) Inventors: Se-Jin Lee; Thanh Huynh, both of Baltimore; Suzanne Sebald, Jessup; Christopher Rankin, Columbia; Edward Hsiao, Baltimore, all of MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/463,931

(22) Filed: Mar. 30, 2000

Related U.S. Application Data

(60) Provisional application No. 60/054,400, filed on Jul. 31, 1997.

(51) Int. Cl.[7] .................. C07K 14/475; C12N 1/21; C12N 5/10; C12N 15/12; C12N 15/63
(52) U.S. Cl. ............. 536/23.5; 536/23.1; 435/320.1; 435/325; 435/252.3; 435/7.1; 530/350; 530/351; 530/387.1; 530/387.9
(58) Field of Search .............. 536/23.1, 23.5; 530/350, 351, 387.1, 387.9; 435/320.1, 325, 252.3, 7.1

(56) References Cited

U.S. PATENT DOCUMENTS 5,194,596 A * 3/1993 Tischer et al.
5,350,836 A * 9/1994 Kopchick et al.

OTHER PUBLICATIONS

M. Bootcov, et al.; MIC–1, a novel macrophage inhibitory cytokine, is a divergent member of the TGF–β superfamily; Proc. Natl. Acad. Sci. USA, Oct. 1997, pp. 11514–11519.
R. Hromas, et al.; PLAB, a novel placental bone morphogenetic protein; Biochimica et Biophysica Acta , 1354; 1997; pp. 40–44.
Vishwas M. Paralkar, et al.; Cloning and Characterization of a Novel Member of the Transforming Growth Factor–β/Bone Morphogenetic Protein Family; The Journal of Biological Chemistry, vol. 273, No. 22, Issue of May 29, 1998; pp. 13760–13767.
N.Q. McDonald, et al.; A structural superfamily of growth factors containing a cysteine knot motif; Cell, May 7, 1993; vol. 73, pp. 421–424, see entire document.
R.M. Lyons, et al.; Transforming growth factors and the regulation of cell proliferation; European Journal of Biochemistry; 1990, vol. 187, pp. 467–473, see entire document.
M.B. Sporn, et al.; Transforming growth factor–beta: new chemical forms and new biological roles. BioFactors, 1988, vol. 1, No. 1, pp. 89–93, see entire document.
J. Massague; The TGF–α family of growth and differentiation factors; Cell; May 22, 1987; vol. 49, pp. 437–438, see entire document.
Benjamin et al., 1998, Development 125:1591–1598.*
Vukicevic et al., 1996, PNAS USA 93:9021–9026.*
Massague, 1987, Cell 49:437–438.*
Pilbeam et al., 1993, Bone 14:717–720.*
Skolnick et al., 2000, Trends in Biotech. 18:34–39.*
Bork, 2000, Genome Research 10:398–400.*
Doerks et al., 1998, Trends in Genetics 14:248–250.*
Smith et al., 1997, Nature Biotechnology 15:1222–1223.*
Brenner, 1999, Trends in Genetics 15:132–133.*
Bork et al., 1996, Trends in genetics 12:425–426.*
Bottner et al., 1999, Gene 237:105–111.*
Hsiao et al., 2000, Mol. Cell. Biol. 20:3742–3751.*
Wells, 1990, Biochemistry 29:8609–8517.*
Ngo et al., 1994, The Protein Foldiong Problem and Tertiary Structure Prediction, Merz et al., eds., Birkhauser, Boston, pp. 492–495.*

* cited by examiner

Primary Examiner—Elizabeth Kemmerer
(74) Attorney, Agent, or Firm—Gray, Cary, Ware & Friedenrich LLP; Lisa A. Haile

(57) ABSTRACT

Growth differentiation factor-15 (GDF-15) polynucleotide sequence and amino acid sequence are provided herein. Also described are diagnostic and therapeutic methods of using GDF-15 polypeptide and polynucleotide sequences.

21 Claims, 1 Drawing Sheet

```
mGDF15.trans
1/1                                                     31/11
AGC GCG CAT GCG CAC CCA AGA GAC TCG TGC CCA CTG GGT CCG GGG CGC TGC TGT CAC CTG
 S   A   H   A   H   P   R   D   S   C   P   L   G   P   G   R   C   C   H   L
61/21                                                   91/31
GAG ACT GTG CAG GCA ACT CTT GAA GAC TTG GGC TGG AGC GAC TGG GTG TTG TCC CCG CGC
 E   T   V   Q   A   T   L   E   D   L   G   W   S   D   W   V   L   S   P   R
121/41                                                  151/51
CAG CTG CAG CTG AGC ATG TGC GTG GGC GAG TGT CCC CAC CTG TAT CGC TCC GCG AAC ACG
 Q   L   Q   L   S   M   C   V   G   E   C   P   H   L   Y   R   S   A   N   T
181/61                                                  211/71
CAT GCG CAG ATC AAA GCA CGC CTG CAT GGC CTG CAG CCT GAC AAG GTG CCT GCC CCG TGC
 H   A   Q   I   K   A   R   L   H   G   L   Q   P   D   K   V   P   A   P   C
241/81                                                  271/91
TGT GTC CCC TCC AGC TAC ACC CCG GTG GTT CTT ATG CAC AGG ACA GAC AGT GGT GTG TCA
 C   V   P   S   S   Y   T   P   V   V   L   M   H   R   T   D   S   G   V   S
301/101                                                 331/111
CTG CAG ACT TAT GAT GAC CTG GTG GCC CGG GGC TGC CAC TGC GCT
 L   Q   T   Y   D   D   L   V   A   R   G   C   H   C   A
```

GROWTH DIFFERENTIATION FACTOR-15

This application is an application filed under 35 U.S.C. 371 from PCT/US98/15455, filed Jul. 24, 1998 which claims benefit from U.S. Provisional application No. 60/054,400 filed Jul. 31, 1997, both of which are incorporated by reference in their entirety.

BACKGROUND OF THE INVENTION

1. Field of the Invention

The invention relates generally to growth factors and specifically to a new member of the transforming growth factor beta (TGF-β) superfamily, which is denoted, growth differentiation factor-15 (GDF-15).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., Nature, 345:167, 1990), Drosophila decapentaplegic (DPP) gene product, which is required for dorsal-ventral axis formation and morphogenesis of the imaginal disks (Padgett, et al., Nature, 325:81–84, 1987), the Xenopus Vg-1 gene product, which localizes to the vegetal pole of eggs (Weeks, et al., Cell, 51:861–867, 1987), the activins (Mason, et al., Biochem, Biophys. Res. Commun., 135:957–964, 1986), which can induce the formation of mesoderm and anterior structures in Xenopus embryos (Thomsen, et al., Cell 63:485, 1990), GDNF, which can promote the survival of motor neurons and midbrain dopaminergic neurons (Lin, et al., Science 260:1130, 1993; Tomae, et al., Nature 373:335, 1995; Beck, et al., Nature 373:339, 1995; Henderson, et al., Science 266:1062, 1994; Van, et al., Nature 373:341, 1995; Oppenheim, et al., Nature 373:344, 1995) and the bone morphogenetic proteins (BMPs, osteogenin, OP-1) which can induce de novo cartilage and bone formation (Sampath, et al., J. Biol. Chem., 265:13198, 1990). The TGF-βs can influence a variety of differentiation processes, including adipogenesis, myogenesis, chondrogenesis, hematopoiesis, and epithelial cell differentiation (for review, see Massague, Cell 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A., and Maston, A., Science 247:1328, 1990). Additional studies by Hammonds, et al., (Molec. Endocrin. 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., Nature 321:779, 1986) and the TGF-βs (Cheifetz, et al., Cell 48:409, 1987), heterodimers have also been detected, and these appear to have different biological properties than the respective homodimers.

Identification of new factors that are tissue-specific in their expression pattern will provide a greater understanding of that tissue's development and function.

SUMMARY OF THE INVENTION

The present invention provides a cell growth and differentiation factor, GDF-15, a polynucleotide sequence which encodes the factor, and antibodies which are bind to the factor. This factor appears to relate to various cell proliferative disorders.

Thus, in one embodiment, the invention provides a method for detecting a cell proliferative disorder which is associated with GDF-15. In another embodiment, the invention provides a method for treating a cell proliferative or immunologic disorder by suppressing or enhancing GDF-15 activity.

In another embodiment, the invention provides a method for identifying GDF-15 receptor polypeptide comprising incubating components comprising GDF-15 polypeptide and a cell expressing a receptor or a soluble receptor under conditions sufficient to allow the GDF to bind to the receptor; measuring the binding of the GDF polypeptide to the receptor; and isolating the receptor. Methods of isolating the receptors are described in more detail in the Examples section.

BRIEF DESCRIPTION OF THE DRAWINGS

FIG. 1 shows the nucleotide (SEQ ID NO:1) and predicted amino acid (SEQ ID NO:2) sequences of human GDF-15.

DETAILED DESCRIPTION OF THE INVENTION

The present invention provides a growth and differentiation factor, GDF-15, and a polynucleotide sequence encoding GDF-15. In one embodiment, the invention provides a method for detection of a cell proliferative or immunologic disorder which is associated with GDF-15 expression or function. In another embodiment, the invention provides a method for treating a cell proliferative or immunologic disorder by using an agent which suppresses or enhances GDF-15 activity.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-15 protein of this invention and the members of the TGF-β family, indicates that GDF-15 is a new member of the family of growth and differentiation factors. Based on the known activities of many of the other members, it can be expected that GDF-15 will also possess biological activities that will make it useful as a diagnostic and therapeutic reagent.

Certain members of this superfamily have expression patterns or possess activities that relate to the function of the nervous system. For example, one family member, namely GDNF, has been shown to be a potent neurotrophic factor that can promote the survival of dopaminergic neurons (Lin, et aL, Science 260:1130, 1993) and motor neurons (Henderson, et al., *Science* 266:1062, 1994; Yan, et al., *Nature* 373:341, 1995; Oppenheim, et al., *Nature* 373:344, 1995). Another family member, namely dorsalin-1, is capable of promoting the differentiation of neural crest cells (Basler, et al., *Cell* 73:687, 1993). The inhibins and activins have been shown to be expressed in the brain (Meunier, et al., *Proc. Nat'l. Acad. Sci.*, USA, 85:247, 1988; Sawchenko, et al., *Nature* 334:615, 1988), and activin has been shown to be capable of functioning as a nerve cell survival molecule (Schubert, et al., *Nature* 344:868, 1990). Another family member, namely GDF-1, is nervous system-specific in its expression pattern (Lee, *Proc. Nat'l. Acad. Sci.*, USA, 88:4250, 1991), and certain other family members, such as Vgr-1 (Lyons, et al., *Proc. Nat'l. Acad. Sci.*, USA, 86:4554, 1989; Jones, et al., *Development*, 111:581, 1991), OP-1 (Ozkaynak, et al., *J. Biol. Chem.*, 267:25220,1992), and BMP-4 (Jones, et al., *Development*, 111:531, 1991), are also known to be expressed in the nervous system.

GDF-15 may also have applications in treating disease processes involving muscle, such as in musculodegenerative diseases or in tissue repair due to trauma. In this regard, many other members of the TGF-β family are also important mediators of tissue repair. TGF-β has been shown to have marked effects on the formation of collagen and to cause a striking angiogenic response in the newborn mouse (Roberts, et al., *Proc. Natl. Acad. Sci., USA* 83:4167, 1986). TGF-β has also been shown to inhibit the differentiation of myoblasts in culture (Massague, et al., *Proc. Natl. Acad. Sci., USA* 83:8206, 1986). Moreover, because myoblast cells may be used as a vehicle for delivering genes to muscle for gene therapy, the properties of GDF-15 could be exploited for maintaining cells prior to transplantation or for enhancing the efficiency of the fusion process.

GDF-15 may also have applications in the treatment of immunologic disorders. In particular, TGF-β has been shown to have a wide range of immunoregulatory activities, including potent suppressive effects on B and T cell proliferation and function (for review, see Palladino, et al., *Ann. N.Y. Acad. Sci.*, 593:181, 1990). GDF-15 may possess similar activities and therefore, may be used as an anti-inflammatory agent or as a treatment for disorders related to abnormal proliferation or function of lymphocytes.

GDF-15 may have applications in promoting various types of wound repair. Many of the members of the TGF-β family are known to be important mediators of tissue repair. TGF-β has been shown to have marked effects on the formation of collagen and causes a striking angiogenic response in the newborn mouse (Roberts, et al., *Proc. Natl. Acad. Sci. USA*, 83:4167, 1986). The BMP's can induce new cartilage and bone growth and are effective for the treatment of fractures and other skeletal defects (Glowacki, et al., *Lancet*, 1:959, 1981; Ferguson, et al., *Clin. Orthoped. Relat. Res.*, 227:265, 1988; Johnson, et al., *Clin. Orthoped. Relat. Res.*, 230:257, 1988). GDF-15 may have similar or related activities and may be useful in repair of tissue injury caused by trauma or burns, for example.

GDF-15 may play a role in regulating various aspects of fertility or maternal or fetal growth or function during pregnancy. Hence, GDF-15 or agents that interfere with GDF-15 function may be useful in contraceptive regimens, in enhancing the success of in vitro fertilization procedures, in preventing premature labor, or in enhancing fetal growth or development.

GDF-15 may also have applications in the treatment of various types of cancer. Several known members of this family can function as tumor suppressors. For example, inhibin alpha has been shown to suppress the development of both gonadal (Matzuk, et al., *Nature* 360:313, 1992) and adrenal (Matzuk, et al., *PNAS*, 91:8817, 1984) tumors. Similarly, MIS has been shown to inhibit the growth of human endometrial and ovarian tumors in nude mice (Donahoe, et al., *Ann. Surg.*, 194:472, 1981). Finally, TGF-β is a potent growth inhibitor for many cell types, and resistance to TGF-β plays an important role in the progression of colon cancer (Markowitz, et al., *Science* 268:1336, 1995).

The term "substantially pure" as used herein refers to GDF-15 which is substantially free of other proteins, lipids, carbohydrates or other materials with which it is naturally associated. One skilled in the art can purify GDF-15 using standard techniques for protein purification. The substantially pure polypeptide will yield a single major band on a non-reducing polyacrylamide gel. The purity of the GDF-15 polypeptide can also be determined by amino-terminal amino acid sequence analysis. GDF-15 polypeptide includes functional fragments of the polypeptide, as long as the activity of GDF-15 remains. Smaller peptides containing the biological activity of GDF-15 are included in the invention.

The invention provides polynucleotides encoding the GDF-15 protein. These polynucleotides include DNA, cDNA and RNA sequences which encode GDF-15. It is understood that all polynucleotides encoding all or a portion of GDF-15 are also included herein, as long as they encode a polypeptide with GDF-15 activity. Such polynucleotides include naturally occurring, synthetic, and intentionally manipulated polynucleotides. For example, GDF-15 polynucleotide may be subjected to site-directed mutagenesis. The polynucleotide sequence for GDF-15 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-15 polypeptide encoded by the nucleotide sequence is functionally unchanged.

Specifically disclosed herein is a partial DNA sequence containing the murine GDF-15 gene. The sequence contains an open reading frame encoding a protein showing significant homology to know members of the TGF-β superfamily. The sequence contains a putative RXXR proteolytic processing site that is followed by a sequence of 115 amino acids that contains all of the hallmarks of the TGF-β superfamily. By analogy with known family members, a dimer of the C-terminal 115 amino acids is predicted to represent the active GDF-15 molecule. Preferably, the human GDF-15 nucleotide sequence is SEQ ID NO:1 or the nucleotide sequence of FIG. 1, having 345 nucleotides.

The polynucleotide encoding GDF-15 includes FIG. 1 (SEQ ID NO:1), as well as nucleic acid sequences complementary to SEQ ID NO:1. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO: 2 under physiological conditions or a close family member of GDF-15. The term "selectively hybridize" refers to hybridization under moderately or highly strigent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The C-terminal region of GDF-15 following the putative proteolytic processing site shows significant homology to the known members of the TGF-β superfamily. The GDF-15 sequence contains most of the residues that are highly conserved in other family members (see FIG. 1).

Minor modifications of the recombinant GDF-15 primary amino acid sequence may result in proteins which have substantially equivalent activity as compared to the GDF-15 polypeptide described herein. Such modifications may be deliberate, as by site-directed mutagenesis, or may be spontaneous. All of the polypeptides produced by these modifications are included herein as long as the biological activity of GDF-15 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-15 biological activity.

The nucleotide sequence encoding the GDF-15 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-15 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989).

The development of specific DNA sequences encoding GDF-15 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for GDF-15 peptides having at least one epitope, using antibodies specific for GDF-15. Such antibodies can be either polyclonally or monoclonally derived and used to detect expression product indicative of the presence of GDF-15 cDNA.

DNA sequences encoding GDF-15 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-15 polynucleotide sequences may be inserted into a recombinant expression vector. The term "recombinant expression vector" refers to a plasmid, virus or other vehicle known in the art that has been manipulated by insertion or incorporation of the GDF-15 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-15 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-15 is expressed from a DNA clone containing the entire coding sequence of GDF-15. Alternatively, the C-terminal portion of GDF-15 can be expressed as a fusion protein with the pro-region of another member of the TGF-β family or co-expressed with another pro-region (see for example, Hammonds, et al., *Molec. Endocrin.* 5:149, 1991; Gray, A., and Mason, A., *Science* 247:1328, 1990).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-15 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The GDF-15 polypeptides of the invention can also be used to produce antibodies which are immunoreactive or bind to epitopes of the GDF-15 polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature* 256:495, 1975; *Current Protocols in Molecular Biology*, Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the GDF-15 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The term "cell-proliferative disorder" denotes malignant as well as non-malignant cell populations which often appear to differ from the surrounding tissue both morphologically and genotypically. Malignant cells (i.e. cancer) develop as a result of a multistep process. The GDF-15 polynucleotide that is an antisense molecule is useful in treating malignancies of the various organ systems. Essentially, any disorder which is etiologically linked to altered expression of GDF-15 could be considered susceptible to treatment with a GDF-15 suppressing reagent. One such disorder is a malignant cell proliferative disorder, for example.

The invention provides a method for detecting a cell proliferative disorder which comprises contacting an anti-GDF-15 antibody with a cell suspected of having a GDF-15 associated disorder and detecting binding to the antibody. The antibody reactive with GDF-15 is labeled with a compound which allows detection of binding to GDF-15. For purposes of the invention, an antibody specific for GDF-15 polypeptide may be used to detect the level of GDF-15 in biological fluids and tissues. Any specimen containing a detectable amount of antigen can be used. The level of GDF-15 in the suspect cell can be compared with the level in a normal cell to determine whether the subject has a GDF-15-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and 201Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-15-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-15-associated disease is effective.

The term "ameliorate" denotes a lessening of the detrimental effect of the GDF-15-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Thus, where a cell-proliferative disorder is associated with the expression of GDF-15, nucleic acid sequences that interfere with GDF-15 expression at the translational level can be used. This approach utilizes, for example, antisense nucleic acid and ribozymes to block translation of a specific GDF-15 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American,* 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-15-producing cell. The use of antisense methods to inhibit the in vitro translation of genes is well known in the art (Marcus-Sakura, *Anal.Biochem.,* 20 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by GDF-15 protein. Such therapy would achieve its therapeutic effect by introduction of the GDF-15 antisense polynucleotide into cells having the proliferative disorder. Delivery of antisense GDF-15 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-15 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector.

Those of skill in the art will know of, or can readily ascertain without undue experimentation, specific polynucleotide sequences which can be inserted into the retroviral genome or attached to a viral envelope to allow target specific delivery of the retroviral vector containing the GDF-15 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-15 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In another embodiment, the invention provides a method for identifying GDF-15 receptor polypeptide comprising incubating components comprising GDF-15 polypeptide and a cell expressing a receptor or a soluble receptor under conditions sufficient to allow the GDF to bind to the receptor; measuring the binding of the GDF polypeptide to the receptor; and isolating the receptor. Methods of isolating the receptors are described in more detail in the Examples section.

In yet another embodiment, the present invention relates to GDF-15 receptor-binding agents that block binding of GDF-15 to their receptors. Such agents could represent research and diagnostic tools in the study of muscle wasting disorder as described above and the development of more effective therapeutics. In addition, pharmaceutical compositions comprising GDF-15 receptor-binding agents may represent effective therapeutics. In the context of the invention, the phrase "GDF-15 receptor-binding agent" denotes a naturally occurring ligand of GDF-15 receptors such as, for example, GDF-15, a synthetic ligand ofGDF-15 receptors, or appropriate derivatives of the natural or synthetic ligands. The determination and isolation of ligands is well described in the art. See, e.g., Lerner, *Trends NeuroSci.* 17:142–146 (1994) which is hereby incorporated in its entirety by reference.

In yet another embodiment, the present invention relates to GDF-15 receptor-binding agents that interfere with binding between GDF-15 receptor and a GDF-15. Such binding agents may interfere by competitive inhibition, by non-competitive inhibition or by uncompetitive inhibition. Interference with normal binding between GDF-15 receptors and one or more GDF-15 can result in a useful pharmacological effect.

In another embodiment, the invention provides a method for identifying a composition which binds to GDF-15 receptors. The method includes incubating components comprising the composition and GDF-15 receptors under conditions sufficient to allow the components to interact and measuring the binding of the composition to GDF-15 receptors. Compositions that bind to GDF-15 receptors include peptides, peptidomimetics, polypeptides, chemical compounds and biologic agents as described above.

Incubating includes conditions which allow contact between the test composition and GDF-15 receptors. Contacting includes in solution and in solid phase. The test ligand(s)/composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science* 241:1077,1988), and the like. Molecular techniques for DNA analysis have been reviewed (Landegren, et al., *Science* 242:229–237, 1988).

To determine if a composition can functionally complex with the receptor protein, induction of the exogenous gene is monitored by monitoring changes in the protein levels of the protein encoded for by the exogenous gene, for example. When a composition(s) is found that can induce transcription of the exogenous gene, it is concluded that this composition(s) can bind to the receptor protein coded for by the nucleic acid encoding the initial sample test composition (s).

Expression of the exogenous gene can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol acetyltransferase gene, an alkaline phosphatase gene, beta-galactosidase,a luciferase gene, a green fluorescent protein gene, guanine xanthine phosphoribosyltransferase, alkaline phosphatase, and antibiotic resistance genes (e.g., neomycin phosphotransferase).

Expression of the exogenous gene is indicative of composition-receptor binding, thus, the binding or blocking composition can be identified and isolated. The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that bind to GDF-15 receptors. Thus, the screening method is also useful for identifying variants, binding or blocking agents, etc., which functionally, if not physically (e.g., sterically) act as antagonists or agonists, as desired.

There are a variety of applications using the polypeptide, polynucleotide, and antibodies of the invention including treatment of cell proliferative and immunologic disorders. In addition, GDF-15 may be useful in various gene therapy procedures.

The following examples are intended to illustrate but not limit the invention. While they are typical of those that might be used, other procedures known to those skilled in the art may alternatively be used.

EXAMPLE 1

Identification and Isolation of a Novel TGF-β Family Member

GDF-15 was isolated from a murine genomic library using human GDF-14 as a probe. Hybridization was carried out in 1.08 M NaCl, 60 mM sodium phosphate, 6 mM EDTA, 48 mM NaOH, 0.5% SDS, 0.2% bovine serum albumin, 0.2% ficoll, and 0.2% polyvinyl pyrrolidone at 65° C. Final washes were carried out in 0.3 M NaCl, 30 mM sodium citrate at 58° C.

The sequence of GDF-15 deduced from analysis of genomic clones is shown in FIG. 1. The sequence contains an open reading frame encoding a protein showing significant homology to know members of the TGF-β superfamily. The sequence contains a putative RXXR proteolytic processing site that is followed by a sequence of 115 amino acids that contains all of the hallmarks of the TGF-β superfamily. By analogy with known family members, a dimer of the C-terminal 115 amino acids is predicted to represent the active GDF-15 molecule.

EXAMPLE 2

Expression of GDF-15

To determine the expression pattern of GDF-15, a Northern blot containing RNA samples prepared from a variety of human tissue (Clontech) is probed with GDF-15. Northern analysis is carried out as described previously (Lee, *Mol. Endocrinol.*, 4:1034, 1990) except that the hybridization is carried out in 5X SSPE, 10% dextran sulfate, 50% formamide, 1% SDS, 200 µg/ml salmon DNA, and 0.1% each of bovine serum albumin, ficoll, and polyvinylpyrrolidone.

Although the invention has been described with reference to the presently preferred embodiment, it should be understood that various modifications can be made without departing from the spirit of the invention. Accordingly, the invention is limited only by the following claims.

---

What is claimed is:

1. An isolated polynucleotide comprising:
   a) SEQ ID NO: 1;
   b) a polynucleotide encoding SEQ ID NO: 2;
   c) a nucleic acid sequence complementary to a) or b);
   d) a polynucleotide fragment of SEQ ID NO: 1 that is at least 15 bases in length;
   e) SEQ ID NO: 1, wherein T is U; or
   f) a polynucleotide encoding SEQ ID NO: 2, wherein T is U.

2. The polynucleotide of claim 1, wherein the polynucleotide is isolated from a mammalian cell.

3. The polynucleotide of claim 2, wherein the mammalian cell is selected from the group consisting of mouse, rat, and human cell.

4. An expression vector including the polynucleotide of claim 1.

5. The vector of claim 4, wherein the vector is a plasmid.

6. The vector of claim 4, wherein the vector is viral.

7. A host cell stably transformed with the vector of claim 4.

8. The host cell of claim 7, wherein the cell is prokaryotic.

9. The host cell of claim 7, wherein the cell is eukaryotic.

10. An isolated polynucleotide according to claim 1, wherein the polynucleotide is selected from:
    a) SEQ ID NO: 1;
    b) a polynucleotide encoding SEQ ID NO:2;
    c) a nucleic acid sequence complementary to a) or b)
    d) SEQ ID NO: 1, wherein T is U; and
    e) a polynucleotide encoding SEQ ID NO:2, wherein T is U.

11. Substantially pure growth differentiation factor-15 (GDF-15) comprising an amino acid sequence as set forth in SEQ ID NO:2.

12. An antibody that specifically binds to the polypeptide of claim 11 or specifically binds to an antigenic fragment thereof.

13. The antibody of claim 12, wherein the antibody is polyclonal.

14. The antibody of claim 12, wherein the antibody is monoclonal.

15. A method of detecting GDF-15 in a sample comprising contacting the antibody of claim 12 with a sample and detecting binding of the antibody.

16. The method of claim 15, wherein the detecting is in vivo.

17. The method of claim 16, wherein the antibody is detectably labeled.

18. The method of claim 17, wherein the detectable label is selected from the group consisting of a radioisotope, a fluorescent compound, a bioluminescent compound and a chemiluminescent compound.

19. The method of claim 15, wherein the detection is in vitro.

20. The method of claim 19, wherein the antibody is detectably labeled.

21. The method of claim 20, wherein the label is selected from the group consisting of a radioisotope, a fluorescent compound, a bioluminescent compound, a chemoluminescent compound and an enzyme.

* * * * *

SEQUENCE LISTING

<160> NUMBER OF SEQ ID NOS: 2

<210> SEQ ID NO 1
<211> LENGTH: 345
<212> TYPE: DNA
<213> ORGANISM: Homo sapiens
<220> FEATURE:
<221> NAME/KEY: CDS
<222> LOCATION: (1)..(345)

<400> SEQUENCE: 1

```
agc gcg cat gcg cac cca aga gac tca tgc cca ctg ggt ccg ggg cgc      48
Ser Ala His Ala His Pro Arg Asp Ser Cys Pro Leu Gly Pro Gly Arg
1               5                   10                  15 tgc tgt cac ctg gag act gtg cag gca act ctt gaa gac ttg ggc tgg      96
Cys Cys His Leu Glu Thr Val Gln Ala Thr Leu Glu Asp Leu Gly Trp
            20                  25                  30 agc gac tgg gtg ttg tcc ccg cgc cag ctg cag ctg agc atg tgc gtg     144
Ser Asp Trp Val Leu Ser Pro Arg Gln Leu Gln Leu Ser Met Cys Val
        35                  40                  45 ggc gag tgt ccc cac ctg tat cgc tcc gcg aac acg cat gcg cag atc     192
Gly Glu Cys Pro His Leu Tyr Arg Ser Ala Asn Thr His Ala Gln Ile
    50                  55                  60 aaa gca cgc ctg cat ggc ctg cag cct gac aag gtg cct gcc ccg tgc     240
Lys Ala Arg Leu His Gly Leu Gln Pro Asp Lys Val Pro Ala Pro Cys
65                  70                  75                  80
```

```
tgt gtc ccc tcc agc tac acc ccg gtg gtt ctt atg cac agg aca gac    288
Cys Val Pro Ser Ser Tyr Thr Pro Val Val Leu Met His Arg Thr Asp
                85                  90                  95 agt ggt gtg tca ctg cag act tat gat gac ctg gtg gcc cgg ggc tgc    336
Ser Gly Val Ser Leu Gln Thr Tyr Asp Asp Leu Val Ala Arg Gly Cys
                100                 105                 110 cac tgc gct                                                        345
His Cys Ala
        115

<210> SEQ ID NO 2
<211> LENGTH: 115
<212> TYPE: PRT
<213> ORGANISM: Homo sapiens

<400> SEQUENCE: 2

Ser Ala His Ala His Pro Arg Asp Ser Cys Pro Leu Gly Pro Gly Arg
1               5                   10                  15

Cys Cys His Leu Glu Thr Val Gln Ala Thr Leu Glu Asp Leu Gly Trp
                20                  25                  30

Ser Asp Trp Val Leu Ser Pro Arg Gln Leu Gln Leu Ser Met Cys Val
            35                  40                  45

Gly Glu Cys Pro His Leu Tyr Arg Ser Ala Asn Thr His Ala Gln Ile
        50                  55                  60

Lys Ala Arg Leu His Gly Leu Gln Pro Asp Lys Val Pro Ala Pro Cys
65                  70                  75                  80

Cys Val Pro Ser Ser Tyr Thr Pro Val Val Leu Met His Arg Thr Asp
                85                  90                  95

Ser Gly Val Ser Leu Gln Thr Tyr Asp Asp Leu Val Ala Arg Gly Cys
                100                 105                 110

His Cys Ala
        115
```